United States Patent [19]

Takasima et al.

[11] Patent Number: 4,892,740
[45] Date of Patent: Jan. 9, 1990

[54] ORALLY ADMINISTRABLE PHARMACEUTICAL PREPARATION OF IMPROVED FLAVORING CHARACTERISTICS

[75] Inventors: Yasuji Takasima, Ageo; Ikuo Koyama, Hasuda; Kimihide Shimano, Ageo; Kaoru Maezuru, Hoya, all of Japan

[73] Assignee: Taisho Pharmaceutical Co., Ltd., Japan

[21] Appl. No.: 147,860

[22] Filed: Jan. 25, 1988

[30] Foreign Application Priority Data

Jan. 3, 1987 [JP] Japan ................................. 62-19828

[51] Int. Cl.⁴ ............................................... A61K 9/28
[52] U.S. Cl. .................................... 424/474; 424/482; 424/489; 424/497
[58] Field of Search ................. 424/81, 497, 493, 495, 424/482, 489

[56] References Cited

U.S. PATENT DOCUMENTS 3,202,731  8/1965  Grevenstuk et al. ............... 424/493
3,968,277  7/1976  Takase ................................. 424/497
4,150,110  4/1979  Yoshida et al. ...................... 424/482
4,443,497  4/1984  Samejima et al. ................... 424/495

Primary Examiner—Thurman K. Page
Assistant Examiner—P. L. Prater
Attorney, Agent, or Firm—Lorusso & Loud

[57] ABSTRACT

An orally administrable pharmaceutical preparation of improved flavoring characteristics composed of a core material containing a drug and a coated layer applied to its surface, said coated layer being composed of a particulate polymeric substance having an average particle diameter of not more than 60 microns and being soluble in gastric juice; and a process for producing said orally administrable pharmaceutical preparation, which comprises causing minute liquid droplets of a volatile liquid containing a drug and optionally a gastric juice-soluble polymeric substance to fall onto a powder bed composed of a gastric juice-soluble particulate polymeric substance having an average particle diameter of not more than 60 microns to coat the surface of the liquid droplets with the gastric juice-soluble particulate polymeric substance, and drying the coated particles.

8 Claims, 1 Drawing Sheet

ORALLY ADMINISTRABLE PHARMACEUTICAL PREPARATION OF IMPROVED FLAVORING CHARACTERISTICS

This invention relates to an orally administrable pharmaceutical preparation having improved flavoring characteristics, and more specifically, it relates to an orally administrable pharmaceutical preparation having improved flavoring characteristics which permits masking of the disagreeable taste of a drug without substantially reducing its inherent bioavailability.

For production of orally administrable pharmaceutical preparations in which the flavoring characteristics of the unpalatable active pharmaceutical ingredients are improved, there have been previously proposed, for example, a method in which such a pharmaceutical ingredient is kneaded into a synthetic polymeric compound or a lipid (see Japanese Patent Publication No. 5487/1980), and a method in which such a pharmaceutical ingredient is encapsulated in microcapsules by coacervation (see U. S. Pat. No. 3,922,379).

According to the former method, the pharmaceutical ingredient is partly exposed on the surface of the resulting preparation, and the method is unsuitable for strongly unpalatable pharmaceuticals. When in the latter coacervation method, a water-soluble base such as ovalbumin is chosen as a shell wall material, the resulting microcapsules may dissolve within the mouth during administration so that the unpalatable drug may be released into the mouth. On the other hand, if a water-insoluble base such as ethyl cellulose is chosen as a shell wall material, the wall material might not dissolve within the stomach or intestines during administration. Consequently, releasing of the drug is inhibited and the bioavailability of the drug is reduced.

It has previously been proposed to wrap vitamin $B_{12}$ with cellulose acetate terephthalate which dissolves within the intestines (see U. S. Pat. No. 3,328,256 corresponding to Japanese Patent Publication No. 33677/1968), vitamin A with gelatin-sugar (see U. S. Pat. No. 3,202,731) or vitamin A with casein (see Japanese Patent Publication No. 9292/1969), all by the so-called powder bed method. No idea has yet been suggested of applying the powder bed method to the improvement of the flavoring characteristics of unpalatable drugs.

The present inventors hit upon an idea of applying the powder bed method to the making of an orally administrable pharmaceutical preparation which contains an unpalatable drug but has improved flavoring characteristics, and investigated on coating materials for application to a core material containing an unpalatable drug and on the particle size of such coating materials. Consequently, they have now succeeded in providing an orally administrable pharmaceutical preparation which contains an unpalatable drug but has markedly improved flavoring characteristics without substantially reducing the inherent bioavailability of the drug.

According to this invention, there is provided an orally administrable pharmaceutcial preparation of improved flavoring characteristics composed of a core material containing a drug and a coating layer applied to its surface, said coating layer being composed of a particulate polymeric substance having an average particle diameter of not more than 60 microns and being soluble in gastric juice.

The orally administrable pharmaceutical preparation of improved flavoring characteristics provided by this invention can be prepared by the so-called "powder bed method" which comprises causing minute droplets of a volatile liquid containing the drug and optionally, the polymeric substance soluble in gastric juice to fall onto a powder bed composed of the gastric juice-soluble particulate polymeric substance and having an average particle diameter of not more than 60 microns thereby to form a coating layer of the particulate polymeric substance on the surface of the liquid droplets, and then drying the coating layer.

Figure 1:
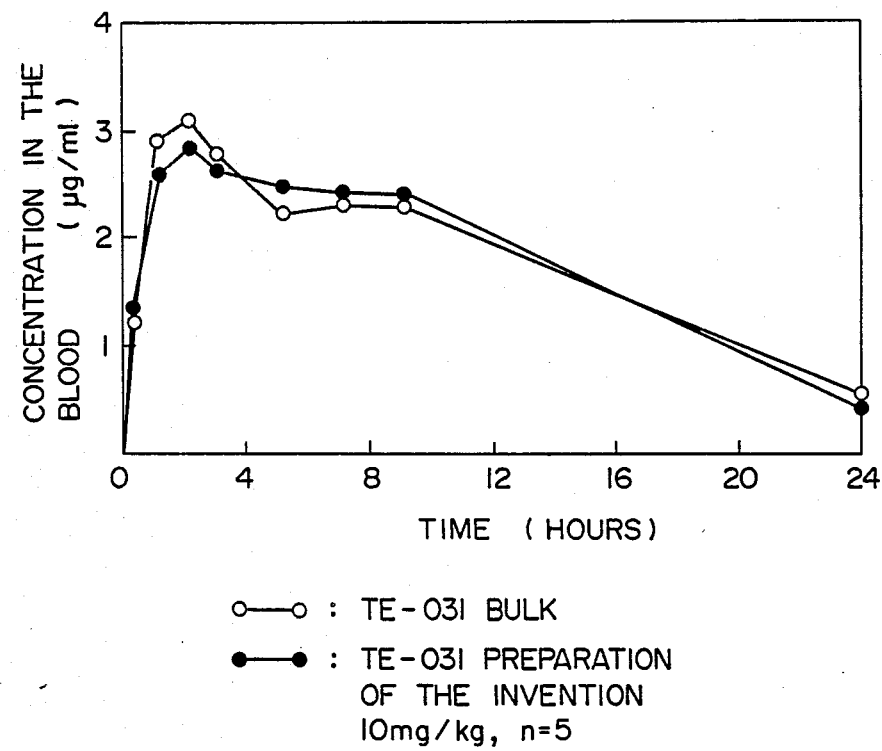
FIG. 1 illustrates that oral delivery of a preparation of methylerythromycin A possessing improved flavoring characteristics is substantially as effective as oral delivery of bulk methylerythromycin A.

The polymeric substance soluble in gastric juice which is used to mask the disagreeable taste of the drug in the core material in this invention is a pharmaceutically acceptable organic polymeric substance which does not dissolve in syrup or saliva but rapidly dissolves in gastric juice. Specific examples include polyvinyl acetal diethylaminoacetate (to be referred to as AEA) and dimethylaminoethyl methacrylate/methacrylic acid copolymer (commercially available under the tradename "Eudragit E").

For use as a powder bed in the powder bed method, the polymeric substance should have an average particle diameter of not more than 60 microns. If its particle size is larger, it is difficult to form a coating layer which is sufficiently dense to mask the disagreeable taste of the drug sufficiently. Preferably, the gastric juice-soluble polymeric substances to be used in the invention have an average particle diameter of 1 to 60 microns, especially 5 to 20 microns.

The drug that can be coated with the above polymeric substance in accordance with this invention may be any drug whose flavoring characteristics are desired to be improved. Examples include macrolide antibiotics, tetracycline antibiotics, chloramphenicol, chlorpromazine hydrochloride, etafenone hyhdrochloride, minaprine hydrochloride, lithium carbonate, thiamine hydrochloride, thiamine nitrate and loxistatin, which are unpalatable. It should be understood however that they are merely illustrative, and the scope of the invention is not at all limited by these specific examples.

The core material may be composed of only the drug. If desired, it may be composed of a mixture of the drug and the same polymeric substance soluble in gastric juice as used in the powder bed or a different polymeric substance soluble in gastric juice. If required, the core material may further contain one or more conventional adjuvants. Examples of the conventional adjuvants include suspending aids or drug-dissolving controlling agents, for example cellulose derivatives such as ethyl cellulose, methyl cellulose, hydroxypropylmethyl cellulose and hydroxypropyl cellulose; and various drug-dissolving controlling agents, for example higher alcohols such as stearyl alcohol, higher fatty acids such as stearic acid, higher fatty acid glycerides such as hardened castor oil, waxes such as carnauba wax and hydrocarbons such as paraffin.

The core material may be in the form of particles. Generally, it is advantageous for the core material to have an average particle diameter at least 10 times as large as the average particle diameter of the gastric juice-soluble polymeric substance to be coated. The optimum particle diameter of the core material may be properly selected, according to the final form of the pharmaceutical preparation, from the range of 50 to 600 microns, preferably 200 to 400 microns. The content of the drug in the core material is not critical, and can be varied as desired. Generally, it may be 5 to 100% by weight, preferably 20 to 80% by weight.

The components forming the core material are dispersed (dissolved or suspended) in a volatile liquid, and caused to fall as minute liquid droplets onto the powder bed composed of the particulate polymeric substance soluble in gastric acid. The volatile liquid is a normally liquid substance having a boiling point of not more than 100° C., preferably not more than 80° C., and can be substantially completely be evaporated under the drying conditions to be described hereinafter. Examples of the volatile liquid include hydrophilic organic solvents such as methanol, ethanol and acetone and oleophilic organic solvents such as hexane and chloroform. These volatile liquids may be used singly or in combination depending, for example, upon the types of the components forming the core material to be dispersed. When a hydrophilic organic solvent is used, water may be added as required.

Dispersing of the core material-forming components in the volatile liquid may be carried out by a known method such as agitation and shaking. The dispersion so prepared may be formed into fine liquid droplets by ordinary methods of forming fine liquid droplets, for example a pressurized spray method, an air current spray method or a rotating spray method. The size of the liquid droplets can be varied depending upon the desired particle diameter of the core material to be formed from them, and any one skilled in the art would be able to determine it from experience by performing a small-scale routine test.

The liquid droplets so formed are caused to fall onto the powder bed composed of the gastric juice-soluble particulate polymeric substance, and coated with the particulate polymeric substance. During the coating procedure, the powder bed may be vibrated to make the adhesion of the powder to the liquid droplets uniform and consequently effect coating more accurately.

As required, conventional adjuvants may also be added as fine particles having the same particle diameter as the gastric juice-soluble polymeric substance to the powder bed. Examples of the adjuvants include cellulose derivatives such as ethyl cellulose, methyl cellulose, hydroxypropylmethyl cellulose and hydroxypropyl cellulose, higher alcohols such as stearyl alcohol, higher fatty acids such as stearic acid, higher fatty acids glycerides such as hardened castor oil, waxes such as carnauba wax and hydrocarbons such as paraffin. The amount of such a conventional adjuvant may generally be not more than 40% by weight, preferably not more than 10% by weight, based on the weight of the gastric juice-soluble particulate polymeric substance.

The core material particles coated with the gastric juice-soluble particulate polymeric substance are separated from the powder bed by optionally sieving them, and then dried. The drying may be carried out by a known method, for example by using a fluidized bed dryer.

The method described above gives a pharmaceutical preparation in which the surface of the core material containing the drug is coated with a coated layer of the gastric juice-soluble particulate polymeric substance. Desirably, the resulting pharmaceutical composition generally has an average particle diameter at least 10 times as large as the average particle diameter of the gastric juice-soluble particulate polymeric substance constituting the coated layer. It is generally not more than 600 microns, preferably 50 to 600 microns, more preferably 200 to 400 microns.

The orally administrable pharmaceutical preparation having improved flavoring characteristics provided by this invention may be formulated into a final solid unit dosage form, such as granules, pellets, capsules, pills, tablets and sugar-coated tablets for administration.

To make the pharmaceutical preparation easy to administer to small children, it is possible to incorporate a sweetening in the pharmaceutical preparation, or formulate it into a dry syrup by coating the sweetening agent further on the preparation.

As demonstrated by the following Examples and Test Examples, the pharmaceutical preparation provided by this invention improves the flavoring characteristics of an unpalatable drug without substantially reducing its inherent bioavailability, and in oral administration, the drug in it does not taste unpalatable.

The following Examples and Test Examples illustrate the present invention more specifically.

EXAMPLE 1

Polyvinyl acetal diethylaminoacetate (AEA for short; 15 g) was dissolved in 700 g of acetone, and 285 g of 6-O-methylerythromycin A (TE-031 for short) was added to this solution to form a uniform suspension. The suspension was dropped at a flow rate of 20 ml/min. onto the center of a disc, 70 mm in diameter, rotating at a speed of 3,000 rpm. The suspension was repelled from the disc by the centrifugal force and scattered as minute liquid droplets. The minute liquid droplets were let fall onto a fluidized powder bed of AEA having an average particle diameter of 16 microns or 32 microns.

The AEA-coated particles in the powder bed were collected by using a 100-mesh sieve, and dried at 40° C. for 4 hours to give a pharmaceutical preparation.

Ninety percent of the resulting particles had a particle diameter distributed within the range of 250 to 420 microns (average particle diameter 300 microns), and contained 39% of TE-031 in the case of using AEA having a particle diameter of 16 microns, and 30% of TE-031 in the case of using AEA having a particle diameter of 32 microns.

EXAMPLE 2

400 g of TE-031 was added to 600 g of ethanol to form a uniform suspension. The resulting suspension was subjected to the same operation as in Example 1 except that AEA having an average particle diameter of 16 microns was used in the powder bed. Ninety percent of the resulting coated particles had a particle diameter distributed within the range of 250 to 420 microns with an average particle diameter being 310 microns. The resulting phamaceutical preparation contained 49.5% of TE-031.

EXAMPLE 3

AEA (10 g) and 10 g of hydroxypropyl cellulose were dissolved in a 1:1 (w/w) mixture of methanol and chloroform, and 200 g of loxistatin was added to the solution to form a uniform suspension. A pharmaceutical preparation was obtained by subjecting the suspension to the same operation as in Example 1 except that AEA having an average particle diameter of 16 microns was used as the powder bed. Ninety percent of the resulting coated particles had a particle diameter within the range of 250 to 420 microns with an average particle diameter being 350 microns. The pharmaceutical preparation contained 30% of the loxistatin.

EXAMPLE 4

Hydroxypropyl cellulose (20 g) was dissolved in 800 g of chloroform, and 200 g of lithium carbonate was added to form a uniform suspension. A pharmaceutical preparation was produced by subjecting the suspension to the same operation as in Example 1 except that a mixture of AEA powder having an average particle diameter of 16 microns and 10% (w/w) carnauba wax (average particle diameter 20 microns) was used as the powder bed.

Ninety percent of the resulting coated particles had a particle diameter distributed within the range of 250 to 420 microns). The pharmaceutical preparation contained 52% of lithium carbonate.

EXAMPLE 5

AEA (20 g) was dissolved in 700 g of ethanol, and 380 g of erythromycin was added to form a uniform solution. A pharmaceutical preparation was produced by subjecting the solution to the same operation as in Example 1 except that AEA having an average particle diameter of 16 microns was used as the powder bed. Ninety percent of the resulting coated particles had a particle diameter within the range of 250 to 420 microns with an average particle diameter being 310 microns). The pharmaceutical preparation contained 42% of erythromycin.

TEST EXAMPLE

Sample preparation

Sugar (800 g) and 2.5 ml of water were added to mg (calculated as TE-031) of each of the three pharmaceutical preparations (AEA coated particles) obtained in Example 1 to prepare syrups.

Sample 1: A syrup containing 50 mg of TE-031 coated with AEA particles having an average particle diameter of 16 microns used as the powder bed.

Sample 2: A syrup containing 50 mg of TE-031 coated with AEA having an average particle diameter of 32 microns used as the powder bed.

Control sample: A syrup containing 50 mg of TE-031 coated with AEA having an average particle diameter of AEA used as the powder bed.

Testing procedure

Ten hours after preparation of the samples, the samples were each administered to a panel of 15 healthy male adults in an amount of 50 mg as TE-031 per individual, and the bitterness of the samples was evaluated by the panel on the following ratings.

The evaluation was performed immediately after administration and 5 minutes after administration. The degree of bitterness was expressed as "not tolerable", "tolerable but bitter" or "not bitter".

Results

The results are shown in Table 1.

TABLE 1

| Sample | Degree of bitterness | Immediately after administration | 5 minutes after administration |
| --- | --- | --- | --- |
| 1 | not tolerable | 0 | 0 |
|   | tolerable but bitter | 0 | 2 |
|   | not bitter | 15 | 13 |
| 2 | not tolerable | 0 | 0 |
|   | tolerable but bitter | 0 | 2 |
|   | not bitter | 15 | 13 |
| control | not tolerable | 2 | 6 |
|   | tolerable but bitter | 5 | 6 |
|   | not bitter | 8 | 3 |

TEST EXAMPLE 2

Test Animals

Five male Beagle dogs weighing 10 kg were used as experimental animals.

Sample

The pharmaceutical preparation obtained in Example 1 (coated particles containing 39% of TE-031 prepared by using AEA powder having an average particle diameter of 16 microns as the powder bed) was used in an amount of 100 mg as TE-031.

Testing procedure

The sample was orally administered together with water to the experimental animals, and the concentration of TE-031 in the blood was measured by the bioassay method.

Then after a period of 10 days during which the sample was not administered, a capsule containing 100 mg of the bulk of TE-031 was orally administered as a control together with water. The concentration of TE-031 in the blood was likewise measured by bioassay.

Results

The results are shown in FIG. 1 (blood level-time characteristic curves). It is seen from FIG. 1 that the TE-031 bulk and the TE-031 preparation in accordance with this invention showed much the same blood level profiles. The highest blood level appeared 2 hours later in both cases. The maximum blood level was 3.06 $\mu$g/ml for the bulk and 2.83 $\mu$g/ml for the preparation of the invention, and no significant difference was seen.

The area below the blood level curve which is an index for bioavailability was 42.42 hr.$\mu$g/ml for the bulk, and 42.65 hr.$\mu$g/ml for the preparation of the invention, and no significant statistical difference could be found between then.

The above results demonstrate that the bioavailability of the pharmaceutical preparation of the invention containing TE-031 is not lowered as compared with the TE-031 bulk.

What is claimed is:

1. An orally administrable pharmaceutical preparation of improved flavoring characteristics composed of a core material containing a drug and a coating layer applied to its surface, said coating layer being composed of a particulate polymeric substance having an average particle diameter of not more than 60 microns and being soluble in gastric juice.

2. The pharmaceutical preparation of claim 1 wherein said gastric juice-soluble polymeric substance is polyvinyl acetal diethylaminoacetate or dimethylaminoethyl methacrylate/methacrylic acid copolymer.

3. The pharmaceutical preparation of claim 1 wherein said gastric juice-soluble polymeric substance has an average particle diameter of 5 to 20 microns.

4. The pharmaceutical preparation of claim 1 which has an average particle diameter of at least 10 times as large as the average particle diameter of said gastric juice-soluble polymeric substance.

5. The pharmaceutical preparation of claim 4 which has an average particle diameter of not more than 600 microns.

6. A unit dosage form prepared from the pharmaceutical preparation of claim 1.

7. The unit dosage form of claim 6 which is a granule, pellet, capsule, pill, tablet, sugar-coated tablet or.

8. A process for producing the orally administrable pharmaceutical preparation of claim 1, which comprises causing minute liquid droplets of a volatile liquid containing a drug and optionally a gastric juice-soluble polymeric substance to fall onto a powder bed composed of a gastric juice-soluble particulate polymeric substance having an average particle diameter of not more than 60 microns to coat the surface of the liquid droplets with the gastric juice-soluble particulate polymeric substance, and drying the coated particles.

* * * * *

UNITED STATES PATENT AND TRADEMARK OFFICE
CERTIFICATE OF CORRECTION

PATENT NO. : 4,892,740

DATED : January 9, 1990

INVENTOR(S) : TAKASIMA et al

It is certified that error appears in the above-identified patent and that said Letters Patent is hereby corrected as shown below:

IN THE SPECIFICATION:

Col. 5, line 42, after "to" insert --50--.

Signed and Sealed this

Twenty-sixth Day of February, 1991

Attest:

HARRY F. MANBECK, JR.

Attesting Officer

Commissioner of Patents and Trademarks

UNITED STATES PATENT AND TRADEMARK OFFICE
CERTIFICATE OF CORRECTION

PATENT NO. : 4,892,740
DATED : January 9, 1990
INVENTOR(S) : TAKASIMA et al

It is certified that error appears in the above-identified patent and that said Letters Patent is hereby corrected as shown below:

ON THE FACE OF THE PATENT:

Under the heading "Foreign Application Priority Data",

"January 3, 1987" should read --January 30, 1987--.

Signed and Sealed this

Nineteenth Day of November, 1991

*Attest:*

HARRY F. MANBECK, JR.

*Attesting Officer*     *Commissioner of Patents and Trademarks*